(12) United States Patent
Uemura

(10) Patent No.: US 10,918,844 B2
(45) Date of Patent: Feb. 16, 2021

(54) NEEDLE-LIKE STRUCTURE AND METHOD FOR MANUFACTURING THE SAME

(71) Applicant: Toppan Printing Co., Ltd., Taito-ku (JP)

(72) Inventor: Daizo Uemura, Taito-ku (JP)

(73) Assignee: Toppan Printing Co., Ltd., Taito-ku (JP)

( * ) Notice: Subject to any disclaimer, the term of this patent is extended or adjusted under 35 U.S.C. 154(b) by 0 days.

(21) Appl. No.: 14/707,496

(22) Filed: May 8, 2015

(65) Prior Publication Data

US 2015/0238741 A1    Aug. 27, 2015

Related U.S. Application Data

(63) Continuation of application No. PCT/JP2013/079897, filed on Nov. 5, 2013.

(30) Foreign Application Priority Data

Nov. 9, 2012    (JP) .............................. JP2012-247528

(51) Int. Cl.
*A61M 37/00* (2006.01)
*B29C 43/04* (2006.01)
(Continued)

(52) U.S. Cl.
CPC ..... *A61M 37/0015* (2013.01); *B29C 33/3892* (2013.01); *B29C 33/42* (2013.01); *B29C 41/085* (2013.01); *B29C 41/12* (2013.01); *B29C 43/04* (2013.01); *A61M 2037/0023* (2013.01); *A61M 2037/0046* (2013.01);
(Continued)

(58) Field of Classification Search
CPC .. A61M 2037/0015; A61M 2037/0023; A61M 2037/003; A61M 2037/0038; A61M 2037/0048; A61M 2037/0053; Y10T 428/24479; Y10T 428/2457; B29C 33/3892; B29C 33/42; B29C 41/085; B29C 41/12; B29C 43/04; B29C 33/3857;
(Continued)

(56) References Cited

U.S. PATENT DOCUMENTS 6,183,434 B1    2/2001    Eppstein
7,828,620 B2    11/2010    Gosain et al.
(Continued)

FOREIGN PATENT DOCUMENTS

CN    1830496 A    9/2006
EP    2 047 882 A1    4/2009
(Continued)

OTHER PUBLICATIONS

Dictionary.com. Definition of "Flush". Accessed Jan. 12, 2016, p. 3.*

(Continued)

*Primary Examiner* — Maria V Ewald
*Assistant Examiner* — Ethan Weydemeyer
(74) *Attorney, Agent, or Firm* — Oblon, McClelland, Maier & Neustadt, L.L.P.

(57) ABSTRACT

A needle-like structure includes projections formed in rows on a substrate and extended in a direction, and needle portions formed on each of the projections such that the needle portions are spaced part from one another.

20 Claims, 11 Drawing Sheets

(51) Int. Cl.
*B29C 41/08* (2006.01)
*B29C 41/12* (2006.01)
*B29C 33/42* (2006.01)
*B29C 33/38* (2006.01)
*B29L 31/00* (2006.01)

(52) U.S. Cl.
CPC .. *A61M 2037/0053* (2013.01); *B29C 33/3857* (2013.01); *B29L 2031/753* (2013.01); *B29L 2031/756* (2013.01); *B29L 2031/7544* (2013.01); *Y10T 428/24479* (2015.01)

(58) Field of Classification Search
CPC ....... B29L 2031/753; B29L 2031/7544; B29L 2031/756
USPC .................................. 604/117, 148; 428/156
See application file for complete search history.

(56) References Cited

U.S. PATENT DOCUMENTS

| | | | |
|---|---|---|---|
| 2005/0118388 A1* | 6/2005 | Kingsford | A61B 17/205 428/99 |
| 2005/0261631 A1* | 11/2005 | Clarke | A61K 9/0021 604/173 |
| 2006/0127465 A1 | 6/2006 | Maenosono et al. | |
| 2006/0163215 A1 | 7/2006 | Maenosono et al. | |
| 2006/0202385 A1 | 9/2006 | Xu et al. | |
| 2008/0051699 A1 | 2/2008 | Choi et al. | |
| 2009/0143749 A1 | 6/2009 | Sugimura et al. | |
| 2009/0292254 A1 | 11/2009 | Tomono | |
| 2009/0292255 A1* | 11/2009 | Tomono | A61M 37/0015 604/173 |
| 2010/0305516 A1* | 12/2010 | Xu | A61M 37/0015 604/272 |
| 2011/0183105 A1* | 7/2011 | Gamo | B82Y 30/00 428/119 |

FOREIGN PATENT DOCUMENTS

| | | |
|---|---|---|
| JP | 05-101449 A | 4/1993 |
| JP | 2002-369816 | 12/2002 |
| JP | 2004-058265 | 2/2004 |
| JP | 2004-265600 A | 9/2004 |
| JP | 2005-021677 | 1/2005 |
| JP | 2005-152180 A | 6/2005 |
| JP | 2005-246810 A | 9/2005 |
| JP | 2006-513811 | 4/2006 |
| JP | 2008-520433 | 6/2008 |
| JP | 2008-279237 | 11/2008 |
| JP | 2009066104 A * | 4/2009 ............ A61M 37/00 |
| JP | 2009-240410 | 10/2009 |
| JP | 2009240410 A * | 10/2009 ........ A61M 37/0015 |
| JP | 2010-046722 | 3/2010 |
| JP | 2012-143579 A | 8/2012 |
| JP | 2012-201103 | 10/2012 |
| KR | 10-0682534 B1 | 2/2007 |
| WO | WO 00/74763 A2 | 12/2000 |
| WO | WO 2008/013282 | 1/2008 |
| WO | WO 2010/140760 A2 | 12/2010 |

OTHER PUBLICATIONS

International Search Report dated Feb. 10, 2014, in PCT/JP2013/079897 filed Nov. 5, 2013 (with English translation).

Extended European Search Report dated May 20, 2016 in Patent Application No. 13853875.6.

Office Action dated Nov. 2, 2016, in Chinese Patent Application No. 201380057160.3, filed Nov. 5, 2013 (with English-language Translation).

Office Communication dated Dec. 20, 2016, in European Patent Application No. 13853875.6, filed Nov. 5, 2013.

Office Action dated Oct. 11, 2017 in Chinese Patent Application No. 201380057160.3 (with English language translation and English translation of categories of cited documents).

Office Action dated Feb. 27, 2018 in Japanese Patent Application No. 2014-545708 (with English language translation), 4 pages.

Office Action dated Sep. 5, 2017 in Japanese Application No. 2014-545708, filed Nov. 5, 2013 (with English-language translation).

Korean Office Action dated Mar. 27, 2020 in Patent Application No. 10-2015-7011104 (with English translation), 9 pages.

* cited by examiner

NEEDLE-LIKE STRUCTURE AND METHOD FOR MANUFACTURING THE SAME

CROSS-REFERENCE TO RELATED APPLICATIONS

The present application is a continuation of International Application No. PCT/JP2013/079897, filed Nov. 5, 2013, which is based upon and claims the benefits of priority to Japanese Application No. 2012-247528, filed Nov. 9, 2012. The entire contents of these applications are incorporated herein by reference.

BACKGROUND OF THE INVENTION

Field of the Invention

The present invention relates to a needle-like structure in which multiple microscopic needle portions are arrayed, and a method for manufacturing the structure.

Discussion of the Background

Recently, a method for directly administering a medicament into the skin captures attention. In the method, the skin is punctured using a needle-like structure having a plurality of microscopic needle portions of a micron order (microneedles) in order to have the medicament efficiently taken into the body. According to this method, a medicament can be easily administered in a subcutaneous manner without using a special machine for medication (see Patent Literature 1).

Each of the needle portions of the needle-like structure is required to have slenderness and a point angle for puncturing the skin, and a length for allowing subcutaneous penetration of a medicinal solution, and thus is desired to have a diameter ranging from several micrometers to several hundred micrometers. It is said that each needle portion should desirably have a length of allowing the needle portion to pass through a cornified layer that is the outermost layer of the skin.

The thickness of the cornified layer is slightly different depending on the site of the human body, but is about 20 μm in average. Beneath the cornified layer, there is an epidermis having a thickness of about 200 μm to 350 μm. Further, beneath the epidermis, there is a dermic layer throughout which capillary vessels are laid. Therefore, in order to have a medicament penetrated through the cornified layer, each needle portion is required to have a length of at least 20 μm or more. For the purpose of blood withdrawal, each needle portion is required to have a length of at least 350 μm or more.

In general, approaches to manufacture such a needle-like structure are made by processing silicon. Silicon is a material widely used for manufacturing MEMS devices or semiconductors. Silicon is inexpensive and has excellent microscopic processability. In a proposed method of manufacturing a needle-like structure using silicon, a silicon dioxide film is formed on both surfaces of a silicon wafer, followed by patterning, crystal anisotropic etching applied from its front surface, and isotropic etching applied from its rear surface. Using this method, a needle portion having, for example, a length of not less than 500 μm and a width of not more than 200 μm can be manufactured. By arranging such needle portions in an array, blood can be more reliably withdrawn (see Patent Literature 2). Similarly, in another proposed method of manufacture, wet etching is applied to a silicon substrate to make use of the difference in etching rate between crystal orientations of a single crystal material of silicon (see Patent Literature 3).

In still another method of manufacturing a needle-like structure, a material other than silicon is used. For example, needle portions are formed on one surface of a machine-processed steel plate by means of wire cutting. In this method, the angle is changed between upward cutting and downward cutting to control the dimension and shape of each needle portion to be formed (see Patent Literature 4).

The material used for configuring a needle-like structure is required to be harmless to the human body in case a broken needle portion has remained in the human body. As such materials, biocompatible materials, including medical silicone resins, maltoses, polylactic acids, and dextrans, are expected to be used (see Patent Literature 5).

Patent Literature 1: U.S. Pat. No. 6,183,434
Patent Literature 2: JP-A-2002-369816
Patent Literature 3: JP-A-2004-058265
Patent Literature 4: JP-A-2006-513811
Patent Literature 5: JP-A-2005-021677

SUMMARY OF THE INVENTION

According to one aspect of the present invention, a needle-like structure includes projections formed in rows on a substrate and extended in a direction, and needle portions formed on each of the projections such that the needle portions are spaced part from one another.

According to another aspect of the present invention, a method for manufacturing a needle-like structure includes forming first linear grooves in a first direction in a surface portion of a substrate such that projections are formed in the first direction, and forming second linear grooves in a surface portion of each of the projections such that the second linear grooves are formed parallel to each other in a second direction perpendicular to the first direction. The forming of the first linear grooves includes grinding the surface portion of the substrate such that the first linear grooves parallel to each other along the first direction are formed, and that the projections each having a triangular cross section in the second direction are formed, and the forming of the second linear grooves includes grinding the surface portion of each projection such that the second linear grooves parallel to each other along the second direction are formed, and that each of the second linear grooves has a depth smaller than a depth of each of the first linear grooves, which forms needle portions each having a triangular cross section in the first direction.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
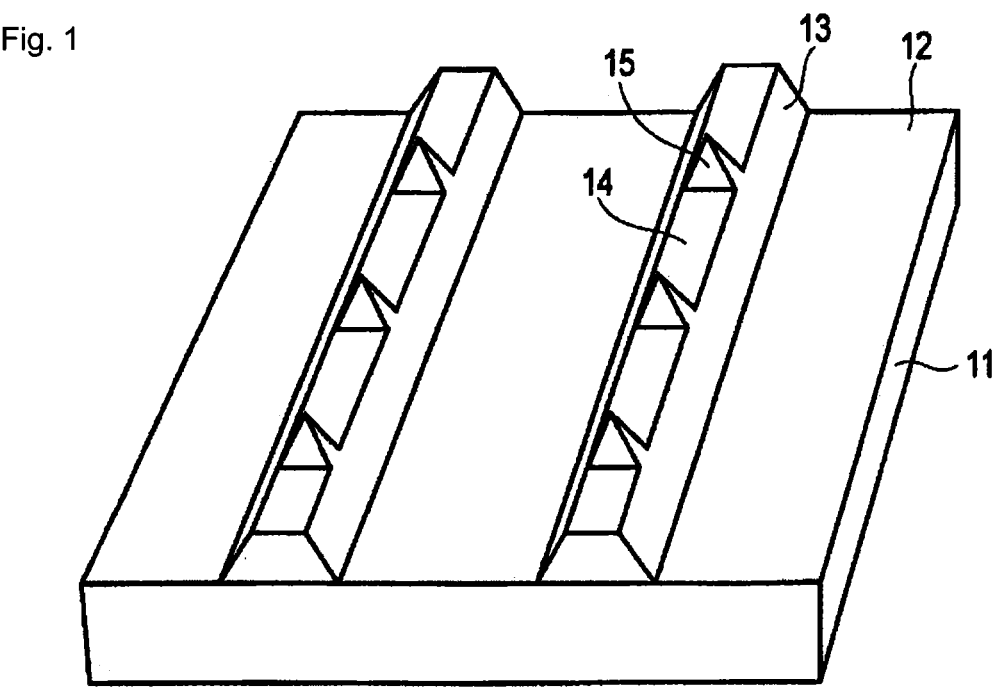
FIG. 1 is a perspective view illustrating a schematic configuration of a needle-like structure (needle-like original plate) related to a first embodiment of the present invention.

The embodiments will now be described with reference to the accompanying drawings, wherein like reference numerals designate corresponding or identical elements throughout the various drawings.

With reference to the drawings, hereinafter are described some embodiments of the present invention.

First Embodiment

Method for Manufacturing a Needle-Like Original Plate

FIG. 1 is a perspective view illustrating a schematic configuration of a needle-like structure (needle-like original plate) related to a first embodiment of the present invention.

In the figure, a reference sign 11 indicates a base substrate. On the substrate 11, multiple rows of projections 13 as sub-patterns are formed so as to be parallel to each other. Each projection 13 is formed thereon with a plurality of four-sided pyramidal needle portions 15.

Each projection 13 as a sub-pattern has a trapezoidal cross section perpendicular to the direction of the rows of sub-patterns. Each needle portion 15 has a triangular cross section both along and perpendicular to the direction of the rows. One side surface of each projection 13 is flush with one side surface of each of the needle portions 15.

For manufacturing the needle-like original plate of FIG. 1, a substrate is processed by grinding. The grinding herein refers to a processing that uses a grinding stone rotating at high speed to scrape an object to be processed with extremely hard and fine abrasive grain that configures the grinding stone. For example, a dicing blade may be used as the grinding stone.

In the grinding of the present embodiment, a dicing blade mounted to an end of a spindle rotating at high speed may be used to form linear grooves in a substrate to be processed. A dicing blade is formed in an outer peripheral portion of a disk-shaped base. It is desirable that the material of the dicing blade has a high hardness. Generally, diamond abrasive grain is used as such a material in many cases. In the present embodiment as well, a diamond wheel may be used, which has a disk-shaped base, with a dicing blade that contains diamond abrasive grain being formed throughout an outer peripheral surface thereof. Diamond wheels are widely used in cutting substrates in the semiconductor industries, and are easily available at low cost.

Usually, a dicing blade has a cross-sectional shape in which a side surface meets a tip surface at an angle of 90° to form a peak. In contrast, the dicing blade used in a method for manufacturing a needle-like original plate of the present embodiment has a side surface, a tip surface, and an inclined surface which is formed in between the side and tip surfaces. The angle of inclination of the inclined surface determines a side-wall angle of each needle portion to be finally formed. Thus, the inclined surface of the dicing blade can control the side-wall angle of each needle portion to be formed.

Figure 2A:
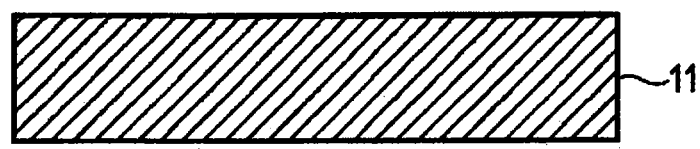
FIG. 2(a)-2(c) show cross-sectional views illustrating a process of manufacturing the needle-like structure illustrated in FIG. 1.
Figure 2B:
Figure 2C:
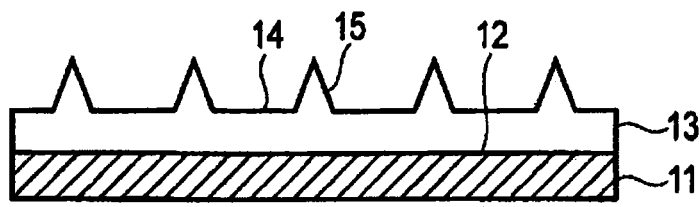

FIGS. 2(a)-2(c) and 3(a)-3(d) each illustrate a process of manufacturing the needle-like structure illustrated in FIG. 1. FIGS. 2(a)-2(c) are cross-sectional views and FIGS. 3(a)-3(d) are perspective views.

First, as shown in FIG. 2(a), the base substrate 11 in a plate-like shape is prepared. The material of the substrate 11 is not limited in m particular but may desirably be selected, taking account of processability or easy availability. Specifically, such materials include: ceramics, such as alumina, aluminum nitride, and machinable ceramics; crystalline materials, such as silicon, silicon carbide, and quartz; organic materials, such as acryl, and polyacetal; metallic materials, such as nickel, and aluminum; and glass.

Figure 3A:
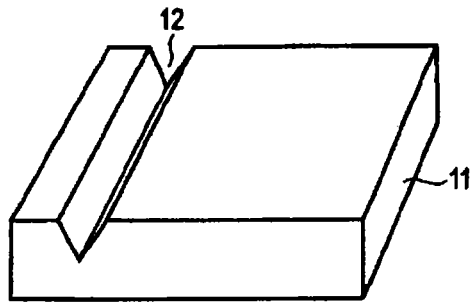
FIG. 3(a)-3(d) show perspective views illustrating a process of manufacturing the needle-like structure illustrated in FIG. 1.

Then, as shown in FIG. 2(b) and FIG. 3(a), a surface of the substrate 11 is diced by the dicing blade in rotation to form a first linear groove 12 along a first direction by a predetermined length. In this case, grinding conditions, such as the number of rotations and the grinding speed of the dicing blade, are not particularly limited, but may desirably be optimized to conditions that ensure excellent processability, taking account of the materials of the dicing blade and the substrate. The first linear groove 12 has a side surface whose inclination coincides with that of the inclined surface formed at an end of the dicing blade.

Figure 3B:
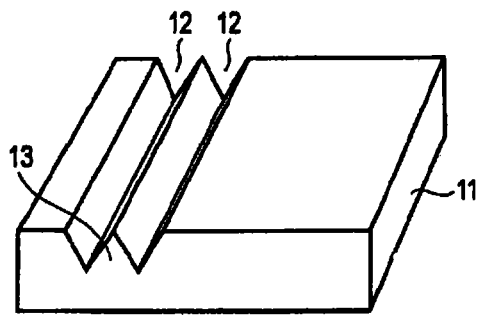

Then, as shown in FIG. 3(b), an adjacent first linear groove 12 is formed so as to be parallel to the first linear groove 12. In other words, using the dicing blade, another first linear groove 12 is machined adjacent to the first linear groove 12. In this case, the dicing blade may be moved relative to the initial first linear groove 12, with the inclined surface being partially overlapped therewith. This can prevent the tip from being flattened, but can ensure a sharp tip, contributing to effectively manufacturing the needle-like structure having excellent puncture properties.

In machining a plurality of first linear grooves 12, it is desirable that the grooves are diced parallel to the first linear groove 12. Adjacently located first linear grooves 12 are formed in this way. In forming adjacently located first linear grooves 12, the inclined surface of the dicing blade in forming one first linear groove 12 is overlapped with the inclined surface of the dicing blade in forming the other first linear groove 12 to form the peak of a tip between the grooves. Thus, as shown in FIG. 3(b), a row of the projection 13 is formed, with its tip being in a sharp shape.

The height of the row of projection 13 is determined by the depth of dicing, the angle of the inclined surface at the end of the dicing blade, and the distance between adjacent first linear grooves 12.

Figure 3C:
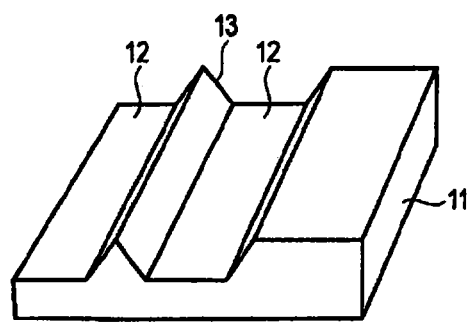
Figure 3D:
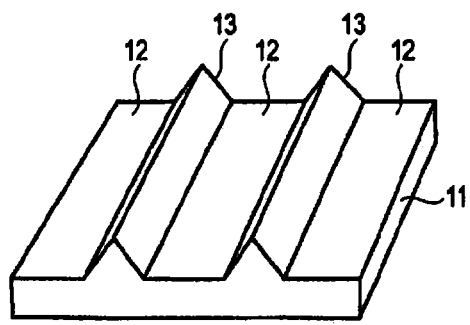

As shown in FIG. 3(c), the dicing blade is translated on both sides of the projection 13 to broaden the width of the first linear groove 12. Further, in a similar manner as mentioned above and as shown in FIG. 3(d), another projection 13 is formed.

Rows of projections 13 are formed in this way by a desired number, resultantly obtaining a substrate with a surface on which multiple rows of projections 13 each having a substantially triangular cross section are formed. In this case, the number of rows of the needle portions in a needle-like structure to be manufactured is determined by the number of rows of projections 13 formed as described above.

Then, as shown in FIG. 2(c) and FIG. 1 previously referred to, a plurality of second linear grooves 14 are provided along a second direction that intersects the first linear grooves 12. In this case, the substrate 11 provided with the first linear grooves 12 is turned, for example, by 90 degrees, so that the second linear grooves 14 can be formed using a method similar to the one used in forming the first linear grooves 12. In this case, the plurality of first linear grooves 12 intersect the plurality of second linear grooves 14 at an angle equal to the angle of the turn of the substrate.

In providing the second linear grooves 14, an adjustment is required to be made in the depth of dicing, the angle of the inclined surface at the end of the dicing blade, and the overlapped distance of the plurality of second linear grooves 14, so that the needle portions to be formed have a height smaller than that of the rows of projections resulting from the formation of the plurality of first linear grooves 12. Further, in a shape resulting from machining the second linear grooves 14 in each row of projection 13, the needle portions 15 are integrated with the row of projection 13. On account of the characteristics of the machining, the needle portions 15 and the rows of projection 13 are formed, with a part of their side faces being flush with each other.

The projection 13 may sometimes remain around the obtained needle portions 15 after forming the second linear grooves 14. When the remained projection 13 is required to be removed, dicing may be performed for the removal of the projections 13.

In order to more sharpen the tip of each of the obtained needle portions 15, isotropic etching may be applied. The term "isotropic etching" herein is defined as including not only the etching that exhibits complete isotropy, but also the etching that slightly exhibits anisotropy but has a strong tendency of isotropy. By applying the isotropic etching, the tip of each of the needle portions 15 can be sharpened without being restricted by the crystal orientations of the substrate.

The method of the isotropic etching can include, but is not particularly limited to, a method performed by means of a dry etching device that uses electric discharge which is based on, for example, RIE, magnetron RIE, ECR, ICP, NLD, microwaves, helicon waves, or the like. Further, for example, dry etching may be performed using a gas, such as $XeF_2$, or the like.

After performing dry etching, the needle portions 15 are each in a shape isotropically shrunk by a constant length. By performing isotropic etching in this way, the shape of each of the needle portions 15 is adjusted to one that enables easier puncture.

As described above, according to the present embodiment, a plurality of first linear grooves 12 are formed along the first distance to form a plurality of projections 13 each having a triangular cross section perpendicular to the first direction. Further, the second linear grooves 14 are formed along the second direction so as to have a smaller depth than the first linear grooves 12. Thus, a plurality of needle portions 15 are formed on each of the projections 13, each needle portion 15 having a triangular cross section perpendicular to the second direction. In this way, a needle-like structure with arrayed needle portions 15 can be fabricated.

The fabricated needle-like structure is different from the one in which the needle portions 15 are simply formed on a flat portion, but is the one in which the needle portions are formed on the projections 13. Accordingly, puncture properties with respect to the skin can be improved. This owes to the fact that the grooves are formed on both sides of each of the needle portions and that the height of the essential projections is made larger. Further, the needle portions 15, which are formed by grinding, not by wet etching, can each be machined so as to have an appropriate shape and dimension. In addition, the first linear grooves 12 are not required to have a strictly controlled depth, but only the second linear grooves 14 are required to have a strictly controlled depth. This leads to an advantage of facilitating machining compared to the case where the needle portions 15 are formed on a flat portion.

Second Embodiment

Method for Manufacturing a Replicated Plate of Needle-Like Body

Subsequently, a filler layer is formed on the needle-like original plate manufactured through the method described above and then the filler layer is separated from the needle-like original plate to thereby form a replicated plate of needle-like body.

Figure 4A:
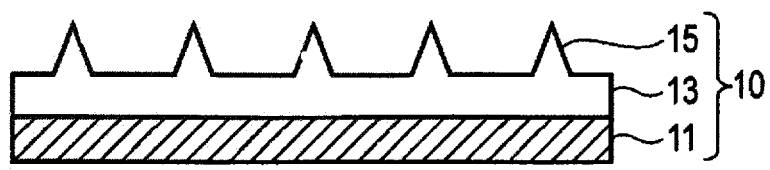
FIG. 4(a)-4(c) show cross-sectional views illustrating a process of manufacturing a replicated plate of needle-like body related to a second embodiment of the present invention.
Figure 4B:
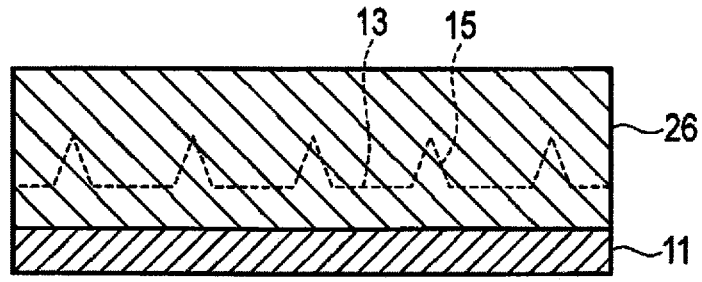
Figure 4C:
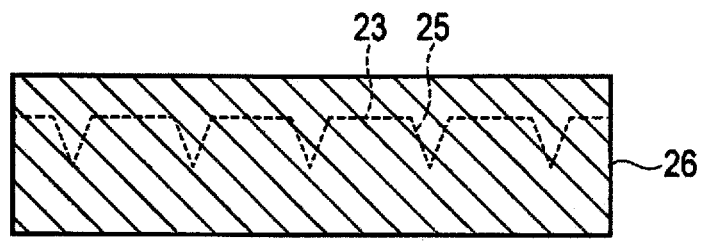

FIGS. 4(a)-4(c) show cross-sectional views illustrating a process of manufacturing the replicated plate of needle-like body.

First, as shown in FIG. 4(a), the original plate 10 of needle-like body as fabricated in the first embodiment is prepared.

Then, as shown in FIG. 4(b), a filler layer 26 is formed on the original plate 10 of needle-like body. The material of the filler layer 26 is not particularly limited, but can be selected taking account of shape-following properties sufficient for exerting the function as a replicated plate, and transferability, durability and releasability in transfer molding described later. For example, the filler layer may be made of nickel, thermosetting silicone resins, and the like. When nickel is selected, the filler layer 26 may be formed by means of plating, PVD, CVD, or the like.

Then, as shown in FIG. 4(c), the original plate 10 of needle-like body is released from the filler layer 26, thereby fabricating a replicated plate. The replicated plate is in a pattern that is an inversion of the original plate 10 of needle-like body. The replicated plate includes a substrate 21 whose surface portion is provided with rows of grooves 23 corresponding to the rows of projections 13, and recesses 25 corresponding to the needle-portions 15, the recesses 25 being provided in each of the grooves 23. The filler layer 26 can be released from the original plate 10 of needle-like body by means of a method that uses a physical release force, or by means of selective etching, or the like.

Thus, according to the present embodiment, an integrally molded replicated plate having high mechanical strength can be fabricated. Using a single replicated plate, a large number of needle-like structures can be manufactured, which contributes to reducing the manufacturing cost and enhancing productivity.

Third Embodiment

Transfer Molding of a Needle-Like Structure

Subsequently, a needle-like body forming material is formed on the replicated plate of needle-like body fabricated through the method described above, and the needle-like body forming material is released from the replicated plate to thereby form a needle-like structure.

Figure 5A:
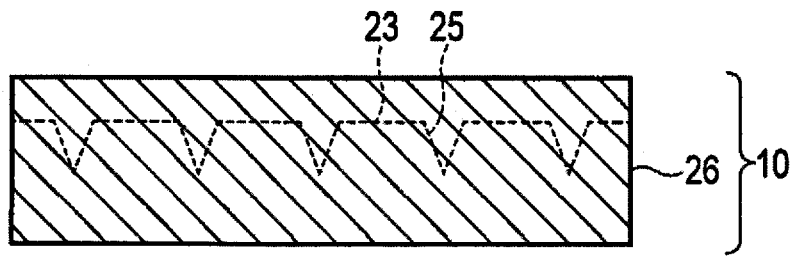
FIG. 5(a)-5(c) show cross-sectional views illustrating a process of transfer molding of a needle-like structure related to a third embodiment of the present invention.
Figure 5B:
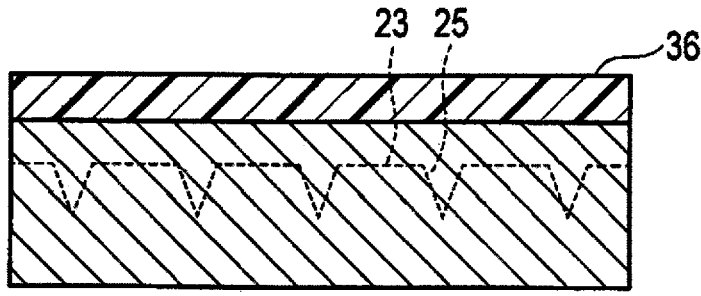
Figure 5C:
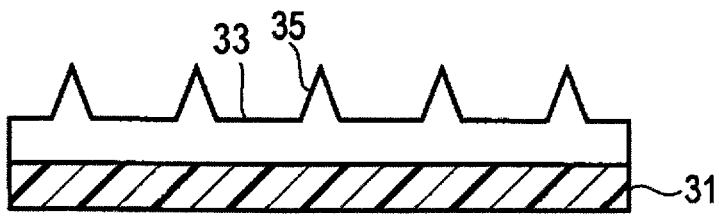

FIGS. 5(a)-5(c) shows cross-sectional views illustrating a process of manufacturing a needle-like structure.

First, as shown in FIG. 5(a), a replicated plate 20 of needle-like body as fabricated in the second embodiment is prepared.

Then, as shown in FIG. 5(b), a needle-like body forming material 36 is filled onto the replicated plate 20. The needle-like body forming material 36 includes, but is not particularly limited to, biocompatible materials, such as medical silicone resins, maltoses, polylactic acids, dextrans, and sugars. Using such materials, a needle-like structure that is applicable to an organism can be formed. Use of the biocompatible materials can exert an effect of being harmless in the event that any one of the needle portions is broken and remained inside the organism.

The method of filling the needle-like body forming material 36 is not particularly limited, but roll molding may be particularly desirable. Besides, imprinting, hot embossing, injection molding, extrusion molding, or casting may be favorably used. When roll molding is used, it is important to fill the material so as to be parallel to the rows of recesses.

Figure 6:
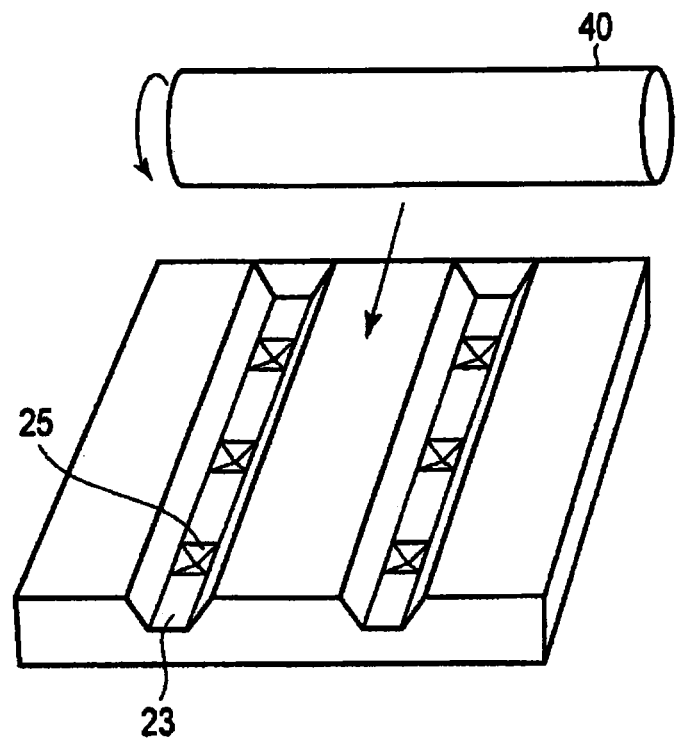
FIG. 6 is a perspective view illustrating a direction of moving a roller in filling a transfer material in a replicated plate of needle-like body.
Figure 7:
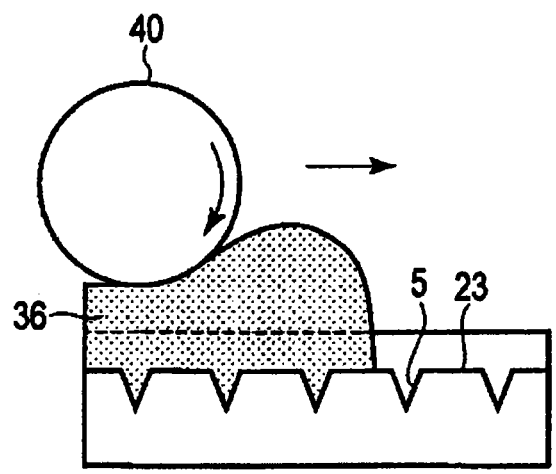
FIG. 7 is a cross-sectional view illustrating a direction of moving a roller in filling a transfer material in a replicated plate of needle-like body.

Therefore, as shown in FIG. 6, the direction of moving a roller 40 is permitted to coincide with a direction in which the grooves 23 are arrayed. Thus, as shown in FIG. 7, when the roller 40 is pressed against the resin 36, the grooves 23 serve as escape routes for the resin. Accordingly, the resin 36 can be favorably filled in the recesses 25. In other words, since the grooves 23 as sub-patterns play a roll of channels for the material, filling properties of the material with respect to the recesses 25 are improved.

Then, the needle-like body forming material 36 is released from the replicated plate 20 to obtain a transfer-molded needle-like structure 30. The obtained needle-like structure 30 has a configuration in which rows of projections 33 are provided on a substrate 31, with a plurality of needle portions 35 being provided on each of the projections 33. In other words, the configuration substantially similar to the one illustrated in FIG. 1 is obtained.

In order to improve the releasability of the replicated plate 20, a release layer for enhancing release effect may be formed on a surface of the replicated plate 20, prior to filling the needle-like body forming material 36. The release layer may be made, for example, of a well-known fluorinated resin. Further, the method for forming the release layer that can be used favorably includes a thin-film forming method, such as PVD, CVD, spin coating, dip coating, or the like.

In this way, according to the present embodiment, filling properties of a molding material can be improved in fabricating a needle-like structure by means of transfer molding. In particular, when a molding material is filled along a direction coinciding with the direction of the rows of grooves 23, the presence of the grooves 23 remarkably improve the filling properties of the material. Accordingly, when the density or the area of the array is increased, sufficient filling properties can be retained.

Based on the first to third embodiments described above, a large number of needle-like structures can be manufactured with good dimensional accuracy. It should be noted that the method for manufacturing a needle-like structure of the present embodiments should not be construed as being limited to the one described in the above embodiments, but may include any other known methods that can be known by analogy from the individual processes.

Figure 8:
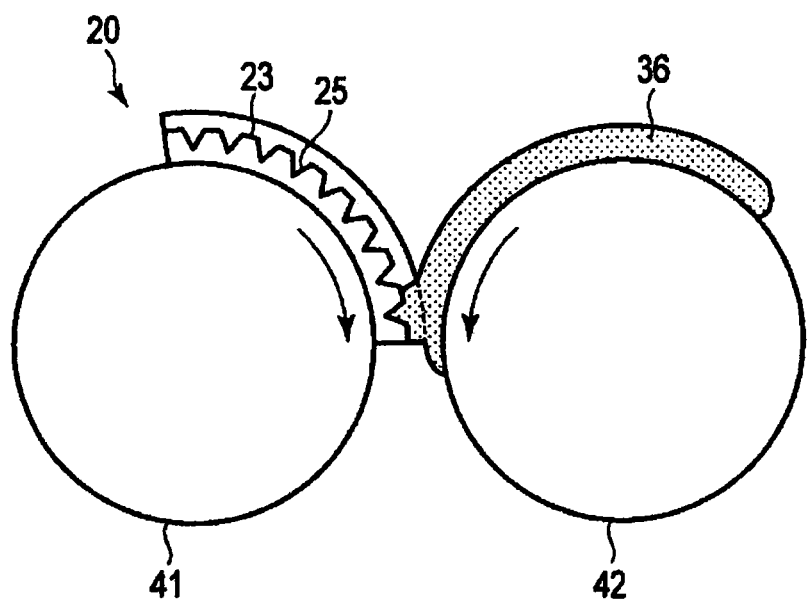
FIG. 8 is a cross-sectional view illustrating an example of transfer molding of a needle-like structure, for explaining a modification.

For example, a method as shown in FIG. 8 may be used as the method of transferring the needle-like structure from the replicated plate. Specifically, in the method, the replicated plate 20 is mounted to one roller 41, and the resin 36 is supplied onto other roller 42, followed by rotating the rollers 41 and 42 in a state of being located close to each other, thereby filling the resin 36. The rows of recesses can be formed throughout the periphery of a roller, and the needle-like structure can be fabricated by means of a roll-to-roll method.

The needle-like structure is more specifically described.

Figure 9A:
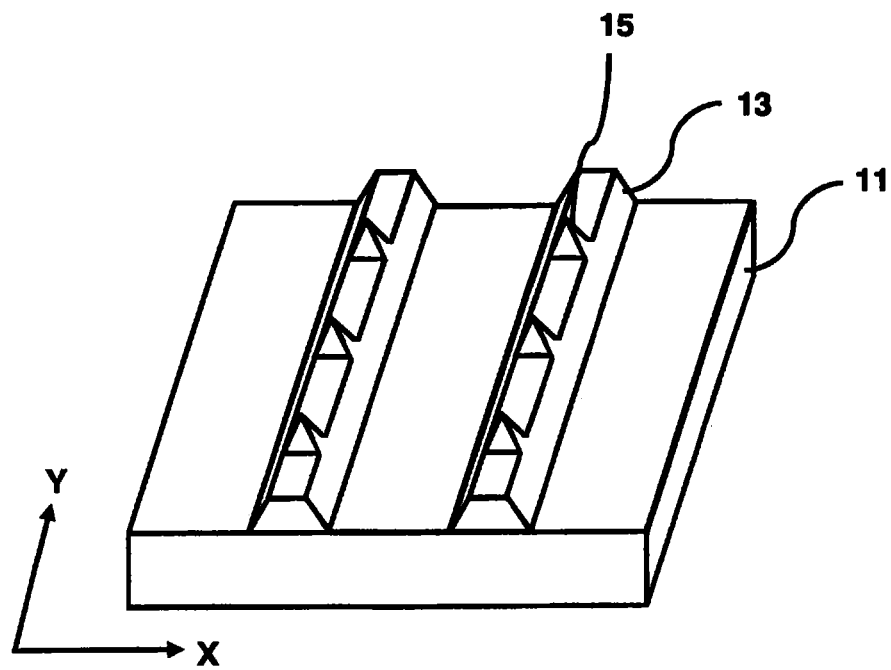
FIG. 9(a)-9(c) show schematic diagrams illustrating a needle-like structure.
Figure 9B:
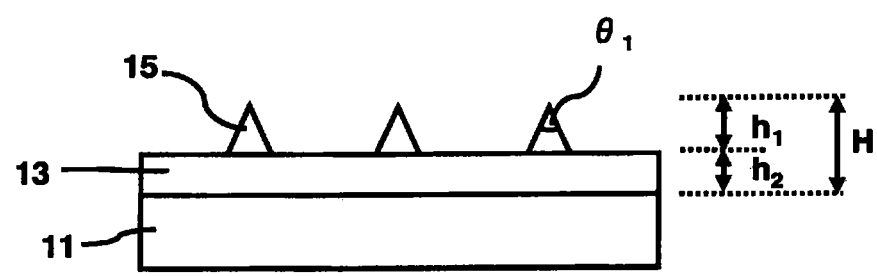
Figure 9C:
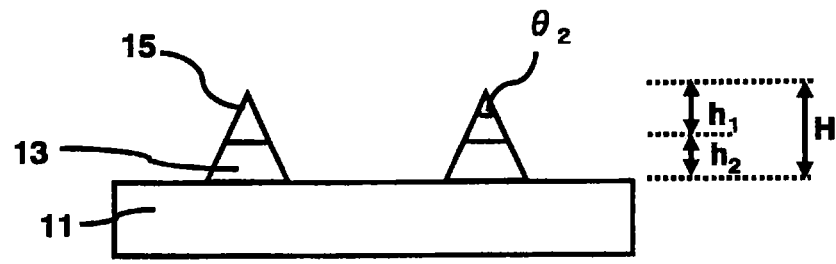

FIGS. 9(a)-9(c) show schematic diagrams of the needle-like structure. FIG. 9(a) shows a perspective view, FIG. 9(b) shows a cross-sectional view as seen from the direction of X, and FIG. 9(c) shows a cross-sectional view as seen from the direction of Y.

In the needle-like structure, it is preferable that the needle portions 15 each have a height $h_1$ which is not less than 100 µm but not more than 2,000 µm. The height of the needle portion is appropriately designed according to the purpose that is an extent of puncture into the skin.

Further, it is preferable that the projections 13 each have a height $h_2$ which is not less than 0.2×H but not more than 0.8H, where H is a sum of the height $h_1$ of the needle portion 15 and the height $h_2$ of the projection 13. If the height $h_2$ of the projection is less than 0.2×H, the effect of the needle-like structure is not necessarily well exerted. On the other hand, if the height $h_2$ of the projection is more than 0.8×H, the strength of the needle-like structure may be lowered.

Further, each of the needle portions 15 has a point angle $\theta_1$ in a cross section as viewed from the direction of X, and a point angle $\theta_2$ in a cross section as viewed from the direction of Y. Preferably, the point angles $\theta_1$ and $\theta_2$ are both not less than 10° but not more than 70°, more preferably, the point angles $\theta_1$ and $\theta_2$ are both not less than 20° but not more than 60°. The point angles of each of the needle portions are appropriately designed, taking account of the extent of puncture into the skin.

In addition, it is preferable that the substrate 11 of the needle-like structure has a size of not less than 1 cm², or more preferably, not less than 5 cm². According to the needle-like structure and the method for manufacturing the needle-like structure, a substrate having a larger size exerts higher effect.

Figure 10A:
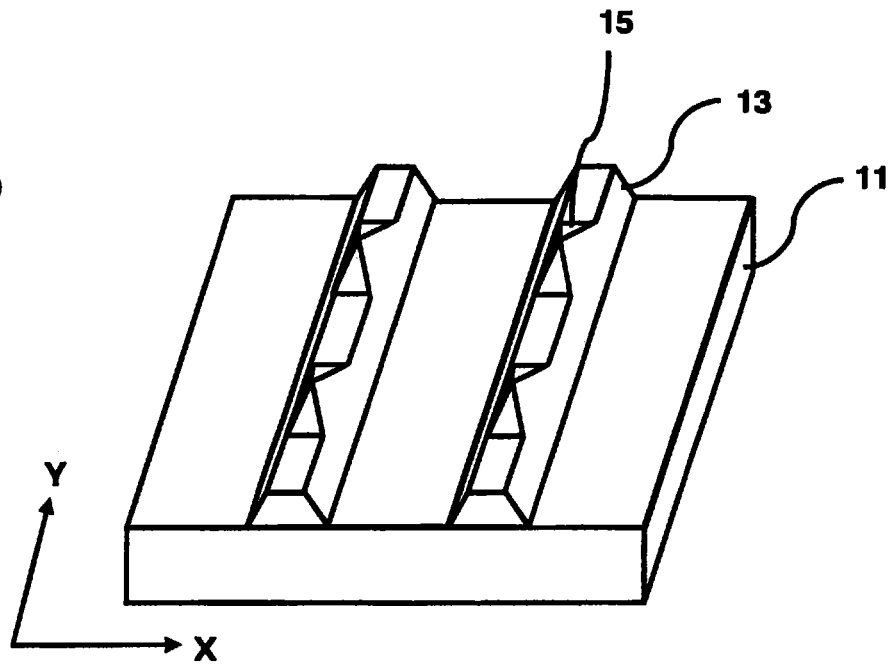
FIG. 10(a)-10(c) show schematic diagrams illustrating a needle-like structure (Modification 1)
Figure 10B:
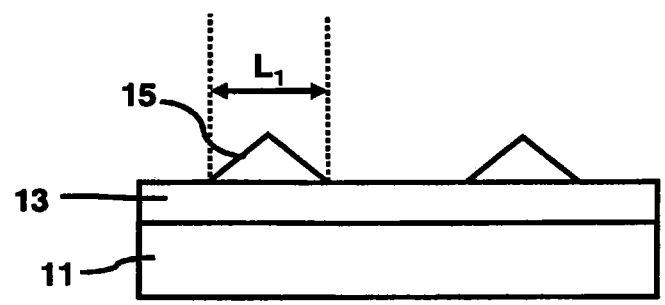
Figure 10C:
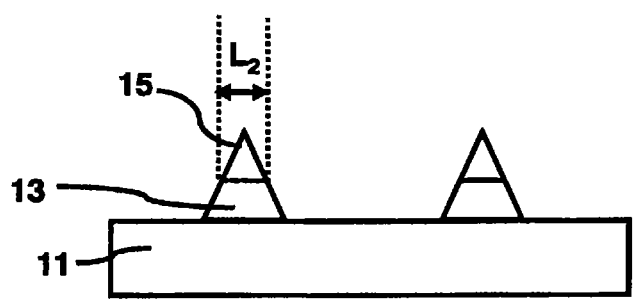

FIGS. 10(a)-10(c) show schematic diagrams illustrating a needle-like structure (Modification 1). FIG. 10(a) shows a perspective view, FIG. 10(b) shows a cross-sectional view as viewed from the direction of X, and FIG. 10(c) shows a cross-sectional view as viewed from the direction of Y.

The needle-like structure (Modification 1) shown in FIGS. 10(a)-10(c) has needle portions that are different not only in the four-sided pyramidal shape but also in the width of the bottom.

In this case, a width $L_1$ of the bottom of the needle portion 15 as cross-sectionally viewed from the direction of X is larger than a width $L_2$ of the bottom of the needle portion 15 as cross-sectionally viewed from the direction of Y ($L_1 > L_2$).

By making larger the width $L_1$ of the needle portion 15 as cross-sectionally viewed from the direction of X than the width $L_2$ of the needle portion 15 as cross-sectionally viewed from the direction of Y, the molding material can be filled much better.

Figure 11A:
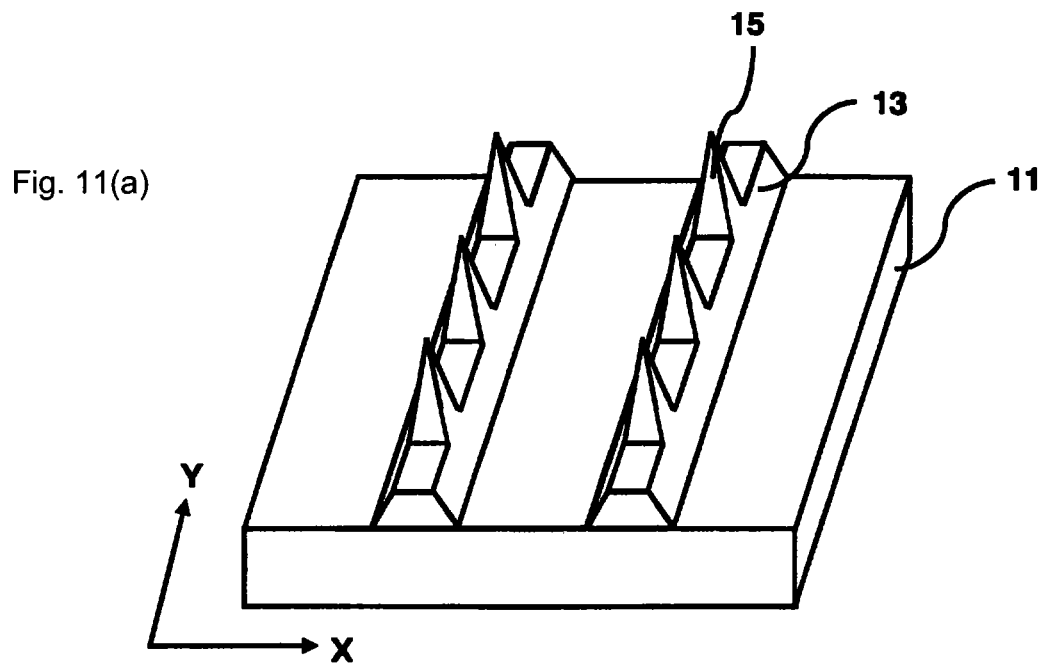
FIG. 11(a)-11(c) show schematic diagrams illustrating a needle-like structure (Modification 2)
Figure 11B:
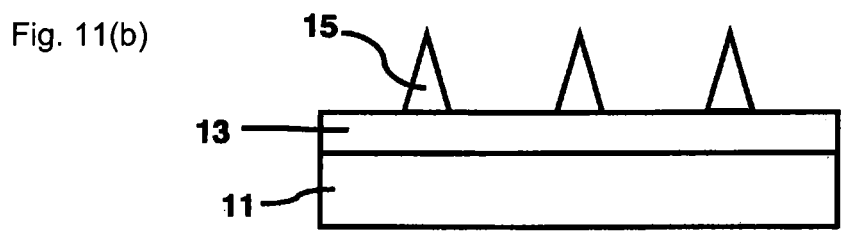
Figure 11C:
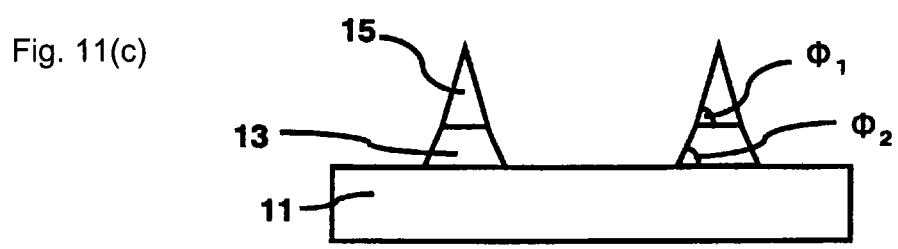

FIGS. 11(a)-11(c) show schematic diagrams illustrating a needle-like structure (Modification 2). FIG. 11(a) shows a perspective view, FIG. 11(b) shows a cross-sectional view as viewed from the direction of X, and FIG. 11(c) shows a cross-sectional view as viewed from the direction of Y.

In the needle-like structure (Modification 2) shown in FIG. 11(a)-11(c), an angle $\Phi_1$ between a side surface of the needle portion 15 and a top surface of the projection 13 as cross-sectionally viewed from the direction of Y, is made larger than an angle $\Phi_2$ between a side surface of the projection 13 and the base substrate 11 as cross-sectionally viewed from the direction of Y ($\Phi_1 > \Phi_2$).

Although the needle-like structure shown in FIGS. 11(a)-11(c) has more number of fabrication steps than the needle-like structure shown in FIGS. 9(a)-9(c), a molding material can be filled much better. When the point angle of each needle portion is made smaller for the purpose of improving puncture properties in relation to the skin, the filling properties of the molding material are further impaired. In this regard, the needle-like structure shown in FIGS. 11(a)-11(c) can eliminate the problem of impairing the filling properties of a molding material.

Figure 12A:
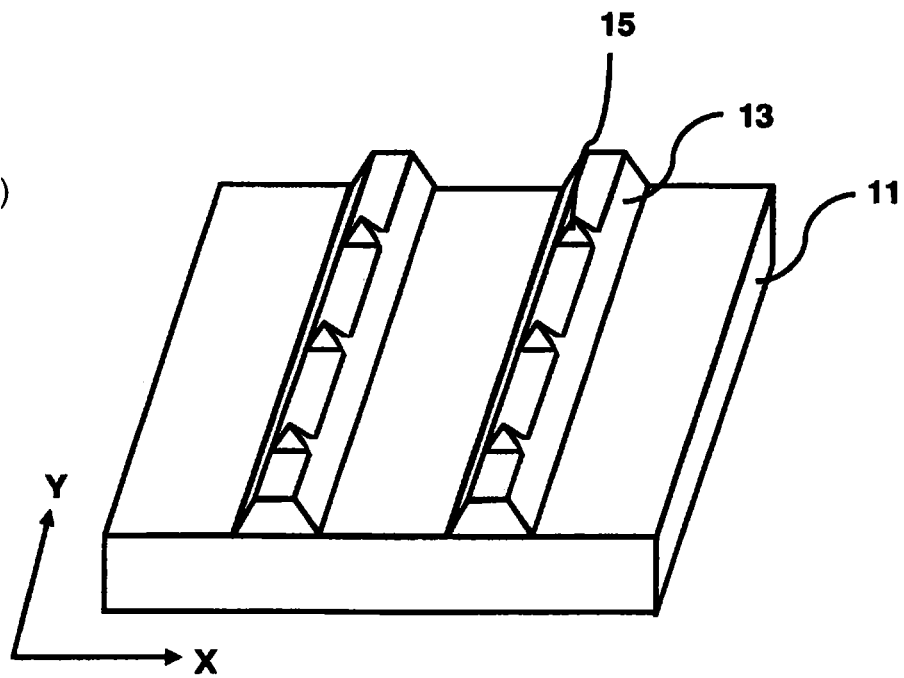
FIG. 12(a)-12(c) show schematic diagrams illustrating a needle-like structure (Modification 3)
Figure 12B:
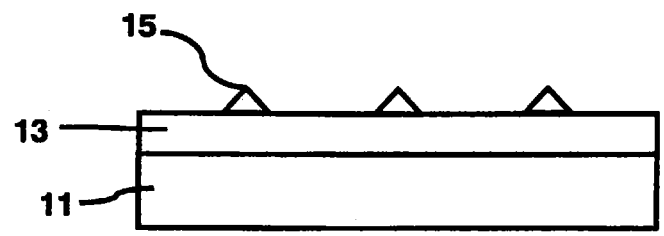
Figure 12C:
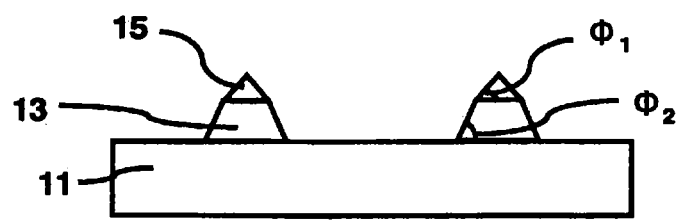

FIGS. 12(a)-12(c) show schematic diagrams illustrating a needle-like structure (Modification 3). FIG. 12(a) shows a perspective view, FIG. 12(b) shows a cross-sectional view as viewed from the direction of X, and FIG. 13(c) shows a cross-sectional view as viewed from the direction of Y.

In the needle-like structure (Modification 3) shown in FIGS. 12(a)-12(c), an angle $\Phi_1$ between a side surface of the needle portion 15 and a top surface of the projection 13 as cross-sectionally viewed from the direction of Y, is made smaller than an angle $\Phi_2$ between a side surface of the projection 13 and the base substrate 11 as cross-sectionally viewed from the direction of Y ($\Phi_1 < \Phi_2$).

Figure 13A:
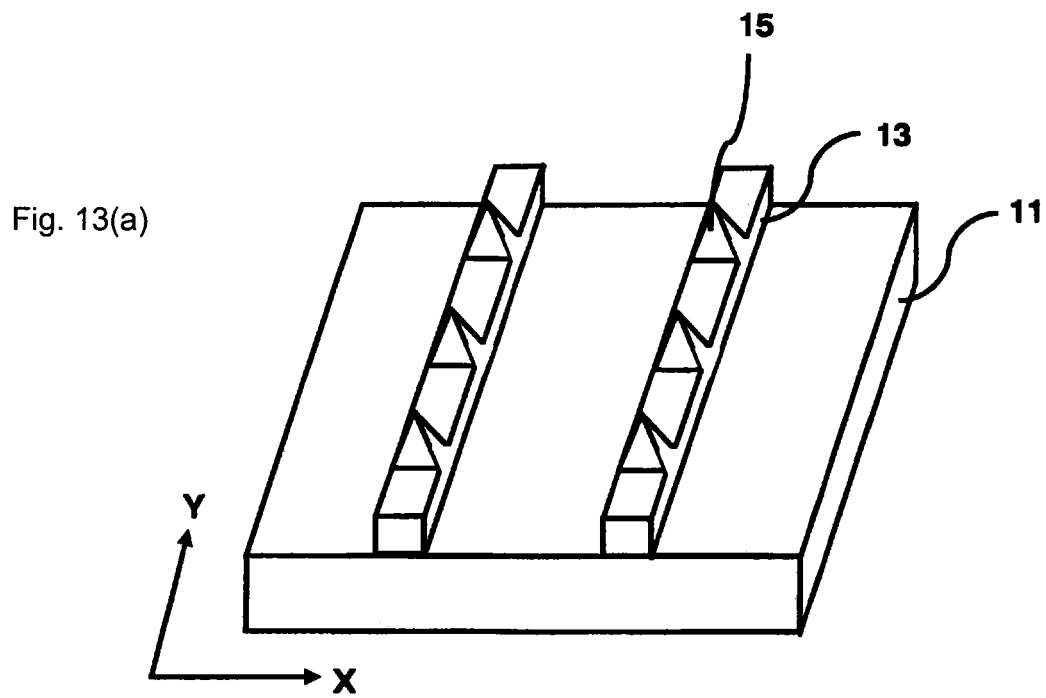
FIG. 13(a)-13(c) show schematic diagrams illustrating a needle-like structure (Modification 4)
Figure 13B:
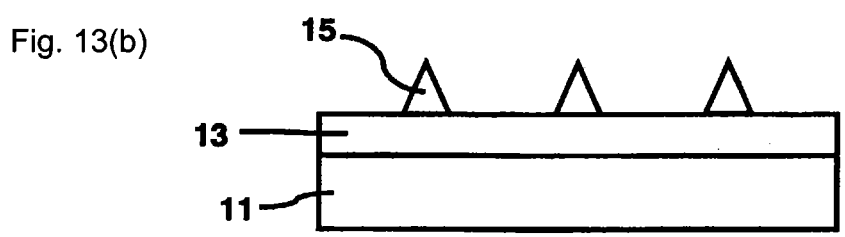
Figure 13C:
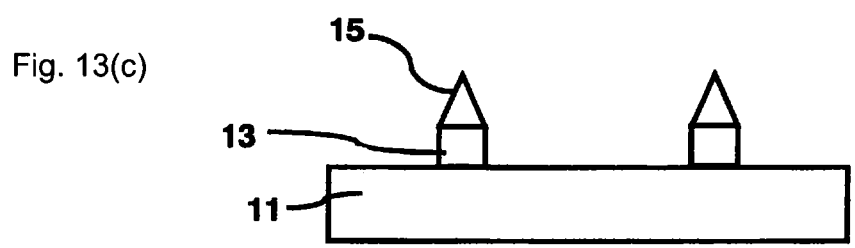

FIGS. 13(a)-13(c) show schematic diagrams illustrating a needle-like structure (Modification 4). FIG. 13(a) shows a perspective view, FIG. 13(b) shows a cross-sectional view as viewed from the direction of X, and FIG. 13(c) shows a cross-sectional view as viewed from the direction of Y.

In the needle-like structure (Modification 4) shown in FIGS. 13(a)-13(c), the projection 13 as cross-sectionally viewed from the direction of Y is in a rectangular shape.

Figure 14A:
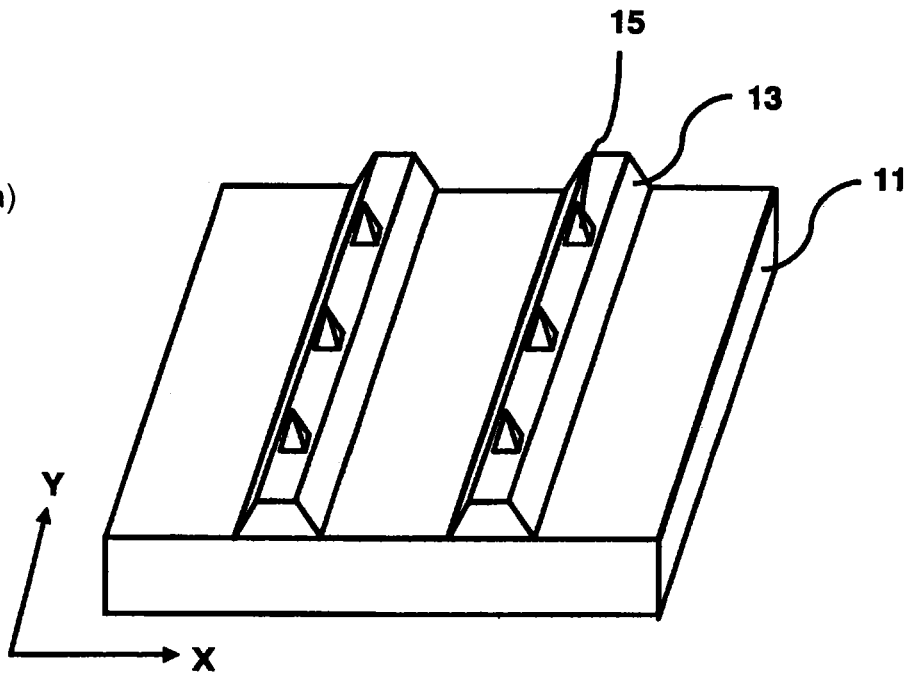
FIG. 14(a)-14(c) show schematic diagrams illustrating a needle-like structure (Modification 5).
Figure 14B:
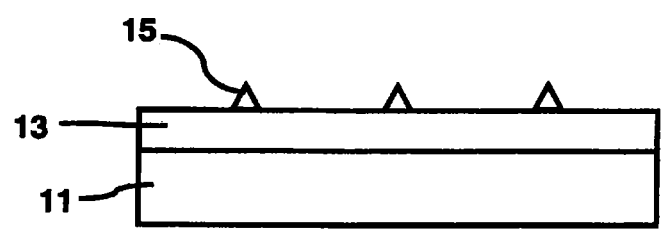
Figure 14C:
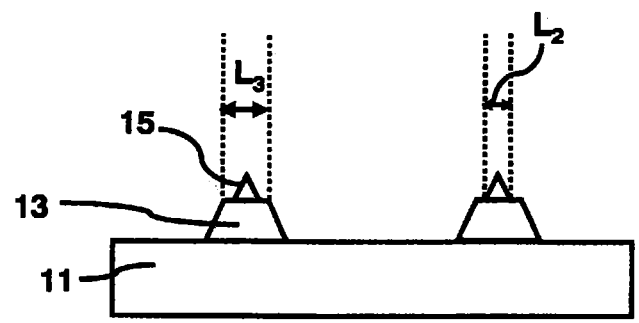

FIGS. 14(a)-14(c) shows schematic diagrams illustrating a needle-like structure (Modification 5). FIG. 14(a) shows a perspective view, FIG. 14(b) shows a cross-sectional view as viewed from the direction of X, and FIG. 14(c) shows a cross-sectional view as viewed from the direction of Y.

In the needle-like structure (Modification 5) shown in FIGS. 14(a)-14(c), a width $L_2$ of the bottom of the needle portion 15 as cross-sectionally viewed from the direction of Y, is made smaller than a width $L_3$ of the bottom of the needle portion as cross-sectionally viewed from the direction of Y.

In the needle-like structure, it is preferable that the width $L_2$ of the bottom of the needle portion 15 as cross-sectionally viewed from the direction of Y ranges from not less than $L_3 \times 0.6$ to not more than $L_3$. Being out of this range, the effect cannot be necessarily sufficiently exerted.

In FIGS. 9(a)-9(c), one side surface of the projection is ensured to be flush with one side surface of each of the needle portions. However, the needle-like structure does not have to necessarily have such side surfaces that are flush with each other. In an embodiment, grinding has been only unidirectionally performed in machining the needle portions to reduce grinding. However, if grinding is performed bidirectionally, the inclination of the side surface of each of the needle portions can be made steeper than the inclination of the side surface of the projection. This is effective when the tip of each needle portion is to be more sharpened.

In the needle-like structure, the first direction in which the first linear grooves are formed does not have to be necessarily perpendicular to the second direction in which the second linear grooves are formed. These directions may only have to intersect with each other.

EXAMPLES

Hereinafter are described more specific examples of the needle-like structure and the method for manufacturing the same, according to the present embodiments.

Example 1

First, referring to FIGS. 3(a)-3(d) again, the process of manufacturing the needle-like original plate is described. The dicing blade used in Example 1 was the one that had been machined so as to possess an inclined surface. The dicing blade had a thickness of 1 mm, and a width of 200 µm in the tip surface, and an angle of 160° between a side surface and the inclined surface. The angle of inclination of the inclined surface determines a side-wall angle of the needle-like structure to be finally formed.

The inclined surface at the tip of the dicing blade in the present example was selected to be 160° in order that each four-sided pyramidal needle portion to be finally formed had a point angle of 40°. The base substrate 11 used was an alumina substrate.

Then, in the dicing using the dicing blade, a step of forming a first linear groove 12 on a surface of the alumina substrate 11 was performed. First, the alumina substrate 11 in a square shape of 100 mm on a side with a thickness of 3 mm was prepared. Then, a surface of the alumina substrate 11 was diced, rotating the dicing blade, to a depth of 300 µm, and a groove having a length of 100 mm was formed.

Through the dicing described above, the first linear groove 12 was formed as shown in FIG. 3(a). The first linear groove 12 had a width of about 418 µm across the opening on top and a depth of 600 µm. The inclination of a side surface of the first linear groove 12 was in conformity with the inclination of the inclined surface formed at the end of the dicing blade, and thus, in the present example, the angle between the surface of the alumina substrate 11 and the side surface of the first linear groove 12 was 110°.

Then, a groove was machined adjacent to the first linear groove 12 using the dicing blade under the same conditions as those in machining the first linear groove 12. In this case, the groove was machined by the dicing blade such that the groove overlapped the first linear groove 12 by a width of 100 µm. The groove was ground parallel to the first linear groove 12. Thus, as shown in FIG. 3(b), a first linear groove 12 having a depth of 600 µm and a length of 100 mm was formed adjacent to the first linear groove 12. Thus, a projection 13, with its tip being in a sharp shape, was formed between the adjacently located linear grooves 12.

In the same manner as in forming the first linear groove 12, first linear grooves 12 were sequentially formed, thereby obtaining a substrate in which a plurality of rows of projections 13 of a desired number were formed. In the present example, a total of 251 first linear grooves 12 were fabricated. As a result, 250 rows of projections 13 were formed.

The rows of projections 13 each had a height of 324 µm, a width of 236 µm in the base, and a point angle of 40°.

Then, the alumina substrate 11 was turned by 90°, and second linear grooves 24 were diced by a number 250 in a manner similar to the one in forming the first linear grooves 12, but with the machining depth being reduced by 162 µm compared to the step of forming the first linear grooves 12. As a result, an original plate 10 of needle-like body was obtained, in which a total of 62,500 needle portions 15 were formed at a pitch of 400 µm on the rows of projections 13, being uniformly arranged on the alumina substrate 11 of 100 mm on a side.

In the present example, the needle portions 15 obtained in this instance were each in a four-sided pyramidal shape with a point angle of 40°, a height of 162 µm, and a width of 118 µm on a side of the bottom.

Referring to FIGS. 4(a)-4(c) again, hereinafter is described a process of manufacturing a replicated plate. First, in order to replicate the fabricated original plate 10 of needle-like body, a replicated plate 20 was made using the original plate 10 of needle-like, followed by transfer molding. First, a nickel film as a filler layer 26 was formed on a surface of the original plate 10 of needle-like body by means of plating. Then, the nickel film 26 was released from the original plate 10 of needle-like body to thereby fabricate the replicated plate 20. The replicated plate 20 was confirmed to have rows of grooves 23 which corresponded to inverted rows of projections 13.

Subsequently, referring to FIGS. 5(a)-5(c) again, a process of manufacturing the needle-like structure is described. First, an epoxy resin as a needle-like body forming material 36 was filled in the replicated plate 20 by means of roll molding. In filling the material, pressure molding was performed in a direction coinciding with the direction of the rows of grooves 23 by means of a laminator device, thereby obtaining a needle-like structure 30 made of the epoxy resin. The obtained needle-like structure made of the epoxy resin is the one in which a number of needle portions 35 are arranged on rows of projections 33. In this case, the projections 33 each had a height $h_2$ of 159 µm. Needle portions 35 each had point angles $\theta_1$ and $\theta_2$ of 40°, a height $h_1$ of 159 µm, and a width of 115 µm on a side of the bottom.

In the obtained needle-like structure, one side surface of each projection 33 was flush with one side surface of each of the needle portions 35. In the obtained needle-like structure, each of the needle portions was confirmed to be molded to the tip thereof.

As a comparative example, a needle-like original plate of the same design (four-sided pyramid having a point angle of 40°, a needle height of 162 µm and a width of 118 µm on a side of the bottom) with no rows of projections 13 was formed, followed by preparing a replicated plate from the original plate. Roll molding was performed under the same conditions as described above, but the filling properties of the epoxy resin were bad, and thus each of the needle portions was not completely formed to the tip thereof. As a result, it was confirmed that the recesses as the sub-patterns arranged in the replicated plate contributed to the improvement of roll molding properties.

Example 2

The replicated plate made of nickel fabricated in Example 1 was used.

As shown in FIGS. 5(a)-5(c), the replicated plate was heated, followed by roll molding to fill a polypropylene resin as the needle-like body forming material 36 into the replicated plate 20. In filling the resin, press molding was performed in a direction coinciding with the direction of the rows of grooves 23 by means of a laminator device. As a result, a needle-like structure 30 made of the polypropylene resin was obtained. The obtained needle-like structure 30 made of the polypropylene resin was the one in which a number of needle portions 35 were arranged on the rows of projections 33. In this case, the projections 33 each had a height $h_2$ of 159 µm. The needle portions 35 each had point angles $\theta_1$ and $\theta_2$ of 40°, a height $h_1$ of 159 µm, and a width of 115 µm on a side of the bottom. In the obtained needle-like structure, one side surface of each projection 33 was flush with one side surface of each of the needle portions 35. In the obtained needle-like structure, each of the needle portions was confirmed to be molded to the tip thereof.

The needle-like structure is applicable to not only medical treatment, but also various fields that require microscopic needle portions. For example, the needle-like structure can be variously applied, such as to MEMS devices, optical members, drug development, cosmetic products, and beauty usages.

In order to mass-manufacture a needle-like structure having a microscopic structure at low cost, transfer molding is effective, as represented by injection molding, imprinting, casting, or the like. In performing molding using any of these methods, an original plate is required to be used, in which a concavo-convex form that is an inversion of a desired form is provided. The manufacturing process is very important in order to form needle portions with tips that are required to be sharpened, at a high aspect ratio (a ratio of a height or a depth of a structure relative to a width thereof).

The method using wet etching based on conventional art makes use of the difference in etching rate between crystal orientations. Therefore, a highly refined single crystal material is required to be used to manufacture the needle-like structure. The taper angle and the point angle of each needle portion are specified by the physical properties of the single crystal material. For this reason, it is difficult to design and manufacture needle portions, each having an appropriate shape and dimension, taking account of the configuration of the skin.

In the method using wire cutting, upward cutting that has reached the peak of a needle portion cannot be immediately followed by downward cutting. Accordingly, as a matter of fact, cutting proceeds in horizontal direction by 1 to 20 µm. Therefore, each of the manufactured needle portions is formed into a pyramidal-trapezoid shape having a flat face at the tip, raising a problem of impairing puncture properties of the needle portions.

In the needle-like structure in which needle portions are arrayed, a material is filled in a replicated plate of needle-like body in performing the transfer molding. However, as the density or the area of the array increases, filling properties of the material are problematically impaired.

In this way, the needle-like structure in which a plurality of microscopic needle portions are arrayed creates difficulty in appropriately designing the dimension and the shape of each of the tips of the needle portions, raising the problem of impairing puncture properties. Further, in filling a material in a replicated plate, there is a problem that filling properties of the material are deteriorated with the increase of the density or the area of the arrays of the replicated plate.

The present invention has been made in order to solve the problems mentioned above and has as its object to provide a needle-like structure which enables appropriate designing of the dimension and the shape of the tip of each of needle portions and can improve the puncture properties of the needle portions. Further, the present invention has another object of providing a method for manufacturing a needle-like structure, which method is able to improve filling properties of a molding material in fabricating a needle-like structure by transfer molding.

The first aspect of the invention is a needle-like structure characterized in that the structure includes a plurality of rows of projections formed being unidirectionally extended on a substrate; and a plurality of needle portions formed being spaced apart on each of the projections.

The second aspect of the invention is the needle-like structure according to the first aspect, characterized in that one side surface of each projection is flush with one side surface of each of the needle portions.

The third aspect of the invention is a method for manufacturing a needle-like structure characterized in that the needle-like structure according to the first aspect is used as an original plate to fabricate a replicated plate from the original plate by means of transfer molding, the replicated plate having recesses corresponding to the projections, and grooves corresponding to the needle portions, and a needle-like structure is fabricated from the replicated plate by means of transfer molding.

The fourth aspect of the invention is the method for manufacturing a needle-like structure according to the third aspect, characterized in that a needle-like structure fabricated from the replicated plate by means of transfer molding is formed of a biocompatible material.

The fifth aspect of the invention is the method for manufacturing a needle-like structure according to the third aspect, characterized in that roll molding is performed by pressing a roller against a needle-like body forming material for filling the replicated plate, and moving the roller in a direction that is the same as a direction in which the recesses extend.

The sixth aspect of the invention is a method for manufacturing a needle-like structure characterized in that the method includes: a step of forming, for a surface of a substrate, a plurality of first linear grooves parallel to each other, the first linear grooves being formed along a first direction by means of grinding, to thereby form a plurality of projections each having a triangular cross section perpendicular to the first direction; and a step of forming, for each of the projections, a plurality of second linear grooves parallel to each other, the second linear grooves being formed along a second direction intersecting the first direction by means of grinding so as to have a depth smaller than that of the first linear grooves, to thereby form a plurality of needle portions each having a triangular cross section perpendicular to the second direction.

The seventh aspect of the invention is the method for manufacturing a needle-like structure according to the sixth aspect, characterized in that, in performing grinding for forming the first and second linear grooves, the method uses a dicing blade having an inclined surface between a side surface and a tip surface.

According to the present invention, the needle portions are not simply formed on a flat portion but are formed on projections. With this configuration, the dimension and the shape of each of the needle portions are appropriately designed, and puncture properties are improved.

Further, with this configuration, filling properties of a molding material can be improved in fabricating the needle-like structure by means of transfer molding. In particular, when a molding material is filled in a direction coinciding with the direction of the recess sub-patterns, the filling properties of the material are remarkably improved by the rows of recess sub-patterns.

DESCRIPTION OF REFERENCE NUMERALS

10 . . . Original plate of needle-like body
11 . . . Alumina substrate (Base substrate)
12 . . . First linear groove
13 . . . Protrusion (sub-pattern)
14 . . . Second linear groove
15 . . . Needle portion
20 . . . Replicated plate of needle-like body
21 . . . Substrate
23 . . . Groove
25 . . . Recess (sub-pattern)
26 . . . Nickel film (filler layer)
30 . . . Needle-like structure
31 . . . Substrate
33 . . . Projection
35 . . . Needle portion
36 . . . Epoxy resin (Needle-like body forming material)
40, 41, 42 . . . Roller Obviously, numerous modifications and variations of the present invention are possible in light of the above teachings. It is therefore to be understood that within the scope of the appended claims, the invention may be practiced otherwise than as specifically described herein.

What is claimed is:

1. A needle-like structure, comprising:
a substrate having an X direction and a Y direction perpendicular to the X direction;
a plurality of projections formed in parallel rows on the substrate and extended in the Y direction; and
a plurality of needle portions formed on each of the projections such that each of the needle portions has a side line extending from a top surface of a respective one of the projections in a cross section of the X direction and forming an angle $\Phi_1$ of less than 90° with respect to the top surface of the respective one of the projections in the cross section of the X direction,
wherein each of the projections has the plurality of needle portions formed in a row and a side line extending from a top surface of the substrate in the cross section of the X direction and forming an angle $\Phi_2$ of less than 90° with respect to the top surface of the substrate in the cross section of the X direction, a tip of each of the needle portions extends in a height direction of the projections, the needle portions are spaced part from one another along the direction in which each of the projections is extended, and the projections and needle portions are formed such that each of the needle portions has a height $h_1$ in a range of from 100 μm to 2,000 μm and that each of the projections has a height $h_2$ which is not less than 0.2×H and not more than 0.8 H, where H is a sum of the height $h_2$ and the height $h_1$ of each needle portion.

2. The needle-like structure according to claim 1, wherein each of the needle portions has a width $L_2$ in a range of $L_3 \times 0.6$ to $L_3$ where the width $L_2$ is a bottom width of each of the needle portions, and the width $L_3$ is a width of each of the projections on which the needle portions are formed.

3. The needle-like structure according to claim 1, wherein the substrate, the projections and the needle portions are made of a material transfer-molded by a replicated plate having a plurality of grooves configured to form the plurality of projections in the parallel rows, and a plurality of recesses configured to form the plurality of needle portions on each of the projections.

4. The needle-like structure according to claim 3, wherein each of the needle portions has a width $L_2$ in a range of $L_3 \times 0.6$ to $L_3$ where the width $L_2$ is a bottom width of each of the needle portions, and the width $L_3$ is a width of each of the projections on which the needle portions are formed.

5. The needle-like structure according to claim 1, wherein each of the needle portions has point angles $\theta_1$ and $\theta_2$, each of which is in a range of from 10° to 70°, where the point angle $\theta_1$ is the point angle in a cross section the Y direction, and the point angle $\theta_2$ in the cross section of the X direction.

6. The needle-like structure according to claim 1, wherein the substrate has a size of not less than 1 cm$^2$.

7. The needle-like structure according to claim 1, wherein the substrate has a size of not less than 5 cm.

8. The needle-like structure according to claim 7, wherein the substrate, the projections and the needle portions are made of a material transfer-molded by a replicated plate having a plurality of grooves configured to form the plurality of projections in the parallel rows, and a plurality of recesses configured to form the plurality of needle portions on each of the projections.

9. The needle-like structure according to claim 7, wherein each of the needle portions has a width $L_2$ in a range of $L_3 \times 0.6$ to $L_3$ where the width $L_2$ is a bottom width of each of the needle portions, and the width $L_3$ is a width of each of the projections on which the needle portions are formed.

10. The needle-like structure according to claim 1, wherein the projections, the substrate, and the needle portions are integrally formed of a resin body.

11. The needle-like structure according to claim 2, wherein each needle portion has point angles $\theta_1$ and $\theta_2$, each of which is in a range of from 10° to 70°, where the point angle $\theta_1$ is the point angle in a cross section of the Y direction, and the point angle $\theta_2$ in the cross section of the X direction.

12. The needle-like structure according to claim 1, wherein each of the needle portions has a triangular cross section in the X direction.

13. The needle-like structure according to claim 1, wherein each of the needle portions has point angles $\theta_1$ and $\theta_2$, each of which is in a range of from 20° to 60°, where the point angle $\theta_1$ is the point angle in a cross section of the Y direction, and the point angle $\theta_2$ in the cross section of the X direction.

14. The needle-like structure according to claim 1, wherein the plurality of projections and the plurality of needle portions are formed such that the angle $\Phi_1$ of the needle portions is greater than the angle $\Phi_2$ of the projections.

15. The needle-like structure according to claim 1, wherein the plurality of projections and the plurality of needle portions are formed such that the angle $\Phi_1$ of the needle portions is smaller than the angle $\Phi_2$ of the projections.

16. The needle-like structure according to claim 1, wherein the plurality of projections and the plurality of needle portions are formed such that the angle $\Phi_1$ of the needle portions is equal to the angle $\Phi_2$ of the projections.

17. The needle-like structure according to claim 5, wherein the plurality of projections and the plurality of needle portions are formed such that the angle $\Phi_1$ of the needle portions is greater than the angle $\Phi_2$ of the projections.

18. The needle-like structure according to claim 5, wherein the plurality of projections and the plurality of needle portions are formed such that the angle $\Phi_1$ of the needle portions is smaller than the angle $\Phi_2$ of the projections.

19. The needle-like structure according to claim 5, wherein the plurality of projections and the plurality of needle portions are formed such that the angle $\Phi_1$ of the needle portions is equal to the angle $\Phi_2$ of the projections.

20. The needle-like structure according to claim 5, wherein the projections, the substrate, and the needle portions are integrally formed of a resin body.

* * * * *